United States Patent [19]

Taylor

[11] Patent Number: 4,991,600

[45] Date of Patent: Feb. 12, 1991

[54] SAMPLING DEVICE

[75] Inventor: James Taylor, Droitwich, England

[73] Assignee: Anchor Products Company, Addison, Ill.

[21] Appl. No.: 438,455

[22] PCT Filed: Apr. 15, 1988

[86] PCT No.: PCT/GB88/00297

§ 371 Date: Dec. 12, 1989

§ 102(e) Date: Dec. 12, 1989

[87] PCT Pub. No.: WO88/07839

PCT Pub. Date: Oct. 20, 1988

[51] Int. Cl.$^5$ .............................................. A61B 10/00

[52] U.S. Cl. ...................................... 128/754; 606/171

[58] Field of Search ............... 128/749, 751, 754, 305; 606/167, 170, 171

[56] References Cited

U.S. PATENT DOCUMENTS 4,282,884 8/1981 Boebel ................................ 128/751

4,733,671 3/1988 Mehl .................................. 128/754

*Primary Examiner*—Randall L. Green

*Assistant Examiner*—Randy Shay

*Attorney, Agent, or Firm*—Jones, Day, Reavis & Pogue

[57] ABSTRACT

A device is disclosed for use in for example obtaining a soft tissue biopsy sample from a patient. In one embodiment the device comprises an outer needle 16 and a sampling needle 18 in coaxial relationship, a handle 34 to which one of the needles e.g. the sampling needle is secured, and a lever arm 36 arranged to enable the other needle e.g. the sample needle 18 to be moved slidingly over the one needle. A spring 40 is arranged to bias the lever arm 36 and hence the sample needle 18 to a predetermined position. In use the needles 16,18 are inserted into a patient and a portion of tissue is trapped in a slot cut into an end portion of the sampling needle 18 as the outer needle 16 slides fully over the sampling needle. The portion of tissue is removed from the device by releasing a catch 38 which causes the outer needle 16 to be drawn back under the influence of the spring to expose the slot in the sampling needle.

15 Claims, 4 Drawing Sheets

SAMPLING DEVICE

BACKGROUND OF THE INVENTION

1. Field of the Invention

This invention relates generally to a device for obtaining a sample of material from within a larger body of the material and more particularly, though not exclusively, concerns a soft tissue biopsy device for surgical use.

During the course of medical treatment it is sometimes necessary for a Doctor, Surgeon, or other qualified medical practitioner to obtain a sample of flesh or other soft tissue from a patient for further diagnostic analysis prior to the patient being treated. The need for a soft tissue sample may arise, for example, when a patient has a suspected tumour, the biopsy analysis identifying whether the tumour is benign or malignant, since this will dictate the most suitable course of treatment.

2. Description of the Related Art

FIG. 1 shows a perspective view of a section through a previously available soft tissue biopsy device generally indicated at 10. The device comprises a main body 12, a plunger 14, a sheath needle 16 and a sampling needle 18. The sampling needle 18 is secured to the plunger 14 and is arranged to pass through the outer sheath needle 16 which is secured to the main body 12. The main body 12 and the plunger 14 are commonly made from a plastics material, and the sheath needle 16 and the sampling needle 18 are made from surgical steel.

The device 10 is supplied in the condition shown in FIG. 1. In this condition the end of the sampling needle 18 is shrouded by the sheath needle 16. Prior to use the surgeon presses the plunger 14 into the main body 12 so that a flange 20 on the plunger 14 passes over an end stop 22 on the main body 12 and continues until it reaches the end face 24. Pressing the plunger 14 into the main body 12 in this way projects the sampling needle 18 forward out of the sheath needle 16. The device 10 is then driven into the patient so that the sampling needle 18 first punctures the soft tissue to be sampled followed by the sheath needle 16.

FIG. 2 shows a detail view of the end of the sheath needle 16 and the sampling needle 18. In FIG. 2(*a*) the sampling needle 18 is shown projecting from the sheath needle 16, and in FIG. 2(*b*) the sampling needle is shown, along with a soft tissue sample 28 retained in a sample collecting slot 26, retracted into the sheath needle 16.

Once the sampling needle and sheath needle have been inserted into the patient, the sampling needle is drawn back into the sheath needle. As the end of the sheath needle passes over the sample collecting slot 26 a soft tissue sample 28 is cut from the patient and retained in the sample collecting slot 26 by the sheath needle 16. To achieve this action, the plunger 18 is drawn back out of the main body until it reaches a stop position where the flange 20 contacts the end stop 22. The sampling needle is thus retracted into the sheath needle 16 along with the soft tissue sample 28 and the device is then removed from the patient prior to retrieval of the sample 28 from the sampling needle 18.

A problem with this arrangement, which the present invention aims to solve, is that manipulation of the sampling device 10 requires the use of at least two hands if the sample is to be successfully retrieved with minimum distress and injury to the patient. The surgeon must first carefully drive the sampling needle 18 and sheath needle 16 into the patient whilst pressing the plunger 14 down into the main body 12. Next, the surgeon must steady the main body and sheath needle with one hand whilst the plunger is drawn back out of the main body to the stop position with the other hand. Finally, as the device is pulled out of the patient, the skin surface surrounding the puncture must be supported to prevent it from becoming distended and causing unnecessary further pain or damage whilst at the same time the plunger must be retained in the stop position to ensure the sample is not lost.

Thus, an undue amount of dexterity is required of the surgeon during what should be a very simple and straightforward procedure. As a result it is not uncommon for an accident to occur. For example, if the surgeon inadvertently fails to retain the plunger in the stop position during the removal of the device from the patient, the sampling needle can slide back out of the sheath needle so that the tissue sample is lost. In the event that the sample is lost, the procedure must be repeated causing undue distress and injury to the patient and additional cost since a new sterile device will have to be used.

SUMMARY OF THE INVENTION

The present invention aims to overcome these and associated problems by providing a soft tissue biopsy device comprising means whereby a soft tissue sample may be collected in a sampling needle using one hand only to operate the device.

According to the invention there is provided a device for obtaining a sample of a material from within a larger body of the material, the device comprising: a substantially cylindrical outer needle arranged to receive substantially co-axially a sampling needle having a sample collecting end portion, the said needles co-operating in use to obtain the sample in the sample collecting end portion;

a handle means to which one of the said needles is removably secured;

a lever arm provided in the handle means and arranged to enable the other of the said needles to be slidingly moved in relation to the one needle by a user in order to obtain the sample; and resilient biasing means provided in the handle means and arranged to bias the lever arm into a predetermined position thereby to position the said needles in a predetermined relationship to each other.

In a preferred embodiment of the invention there is provided a soft tissue biopsy device comprising: a sheath needle, a sampling needle, a handle which fits comfortably into a human hand, a sheath needle driving arrangement enclosed by the handle and including an actuating lever arm extending from the handle, and a catch arrangement for releasably locking the sheath needle over the sampling needle.

BRIEF DESCRIPTION OF THE DRAWINGS

In order that the invention might be clearly understood exemplary embodiments will hereinafter be described with reference to the accompanying drawings in which.

DESCRIPTION OF THE PREFERRED EMBODIMENTS

Figure 3:
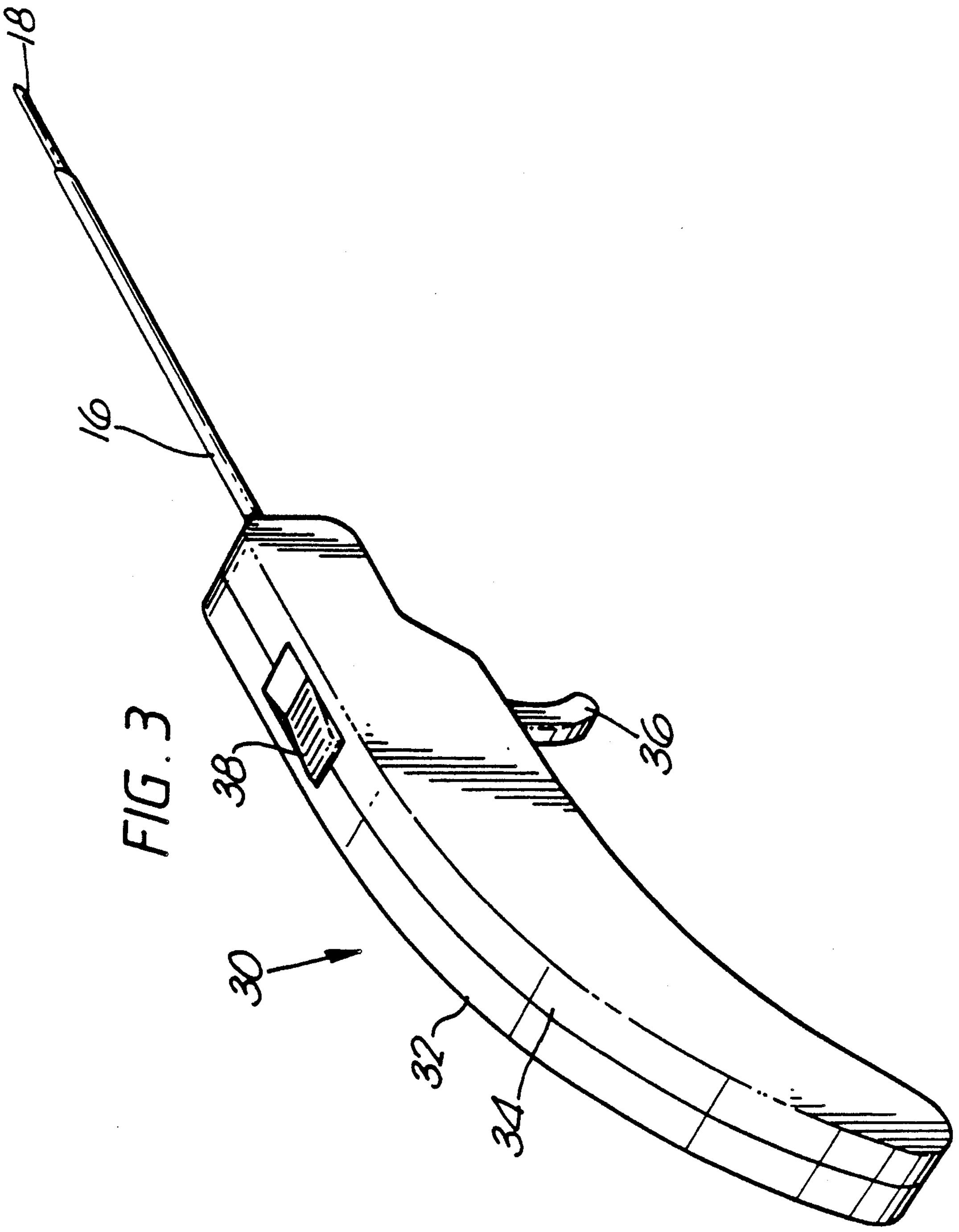
FIG. 3 shows an assembled soft tissue biopsy device in accordance with a first embodiment of the present invention.

Referring now to FIG. 3, the soft tissue biopsy device, generally indicated at 30, comprises a handle formed from two handle sides 32,34, a lever arm 36, a catch 38, and a sheath needle 16 and sampling needle 18 which correspond to similar parts in the described prior art.

Figure 1:
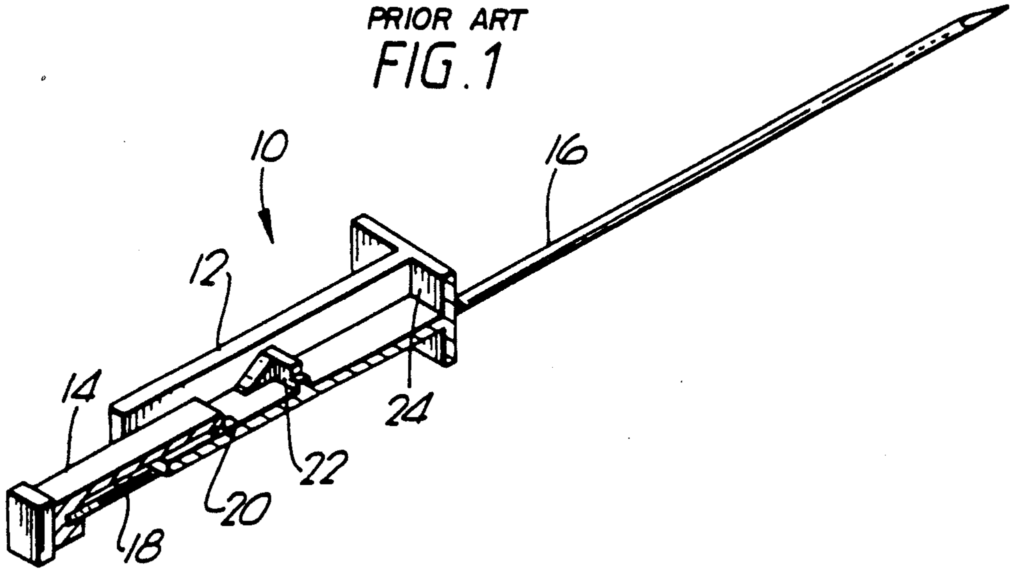
FIG. 1 shows a soft tissue biopsy device in accordance with the prior art.
Figure 2A:
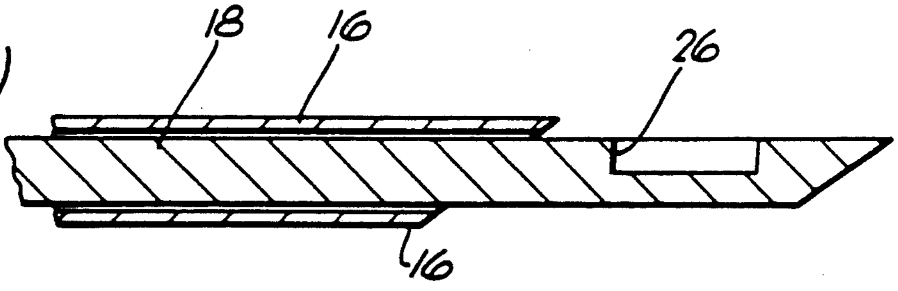
FIG. 2 shows detail views of (a) a sampling needle projecting from a sheath needle, and (b) the sampling needle retracted into the sheath needle.
Figure 2B:
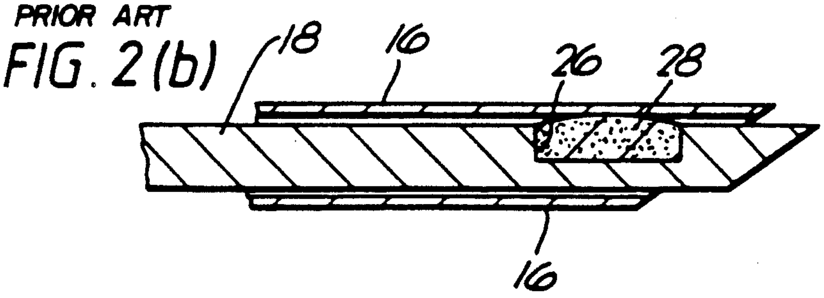

The sample collection action provided by the co-operation of the sheath needle 16 and the sampling needle 18 is similar to that described for the prior art, with reference to FIG. 2, that is to say the sampling needle 18 initially projects from the sheath needle 16, and is initially driven into the patient. The sheath needle can then be driven over the sampling needle by a lever mechanism under the control of the user in a manner described hereinbelow, and the soft tissue sample will be contained in the sample collecting slot 26 prior to removal of the device from the patient.

Figure 4:
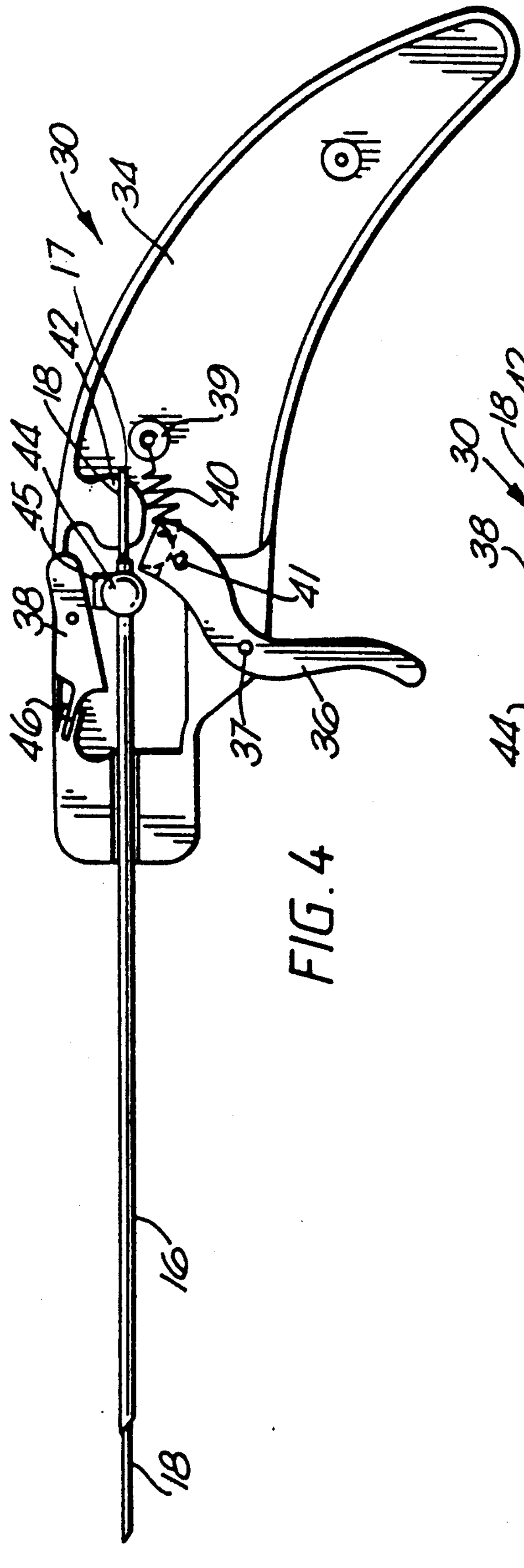
FIG. 4 shows a schematic view of the device in FIG. 3, partly assembled, in a position prior to use.

Referring now to FIG. 4 which shows a side view of the device 30 with the handle side 32 removed. The lever mechanism comprises the lever arm 36 which pivots about a pivot pin 37, and a spring 40 secured to a support column 39 on the handle side 34 and to a retaining pin 41 on the lever arm 36. The sampling needle 18 may be removably secured by any known method to a block 42 moulded into the handle side 34 although it is preferred that the securing method is such as to facilitate replacement of the needles after use. Thus, for example the end portion 17 of the sampling needle may be bent so that it extends below the block 42 whilst an adjacent portion of the sampling needle is received in the block. Another example would be to use a bayonet type arrangement to secure the sampling needle to the block. The sheath needle 16 includes a ball 44 and optionally includes a polarizing fin 45 designed to co-operate with the end of the lever arm 36 to ensure correct orientation of the sheath needle relative to the sampling needle in use. The end of the lever arm 36 above the retaining pin 41 is arranged to co-operate with the ball 44 and polarizing fin 45 when driving the sheath needle over the sampling needle 18, and is formed with a recessed socket (shown in phantom in FIG. 4) for engaging the ball 44 as the lever arm 36 is pivoted to advance the sheath needle 16 and slots in front of and behind the socket for accommodating the needle and polarizing fin on either side of the ball.

Figure 5:
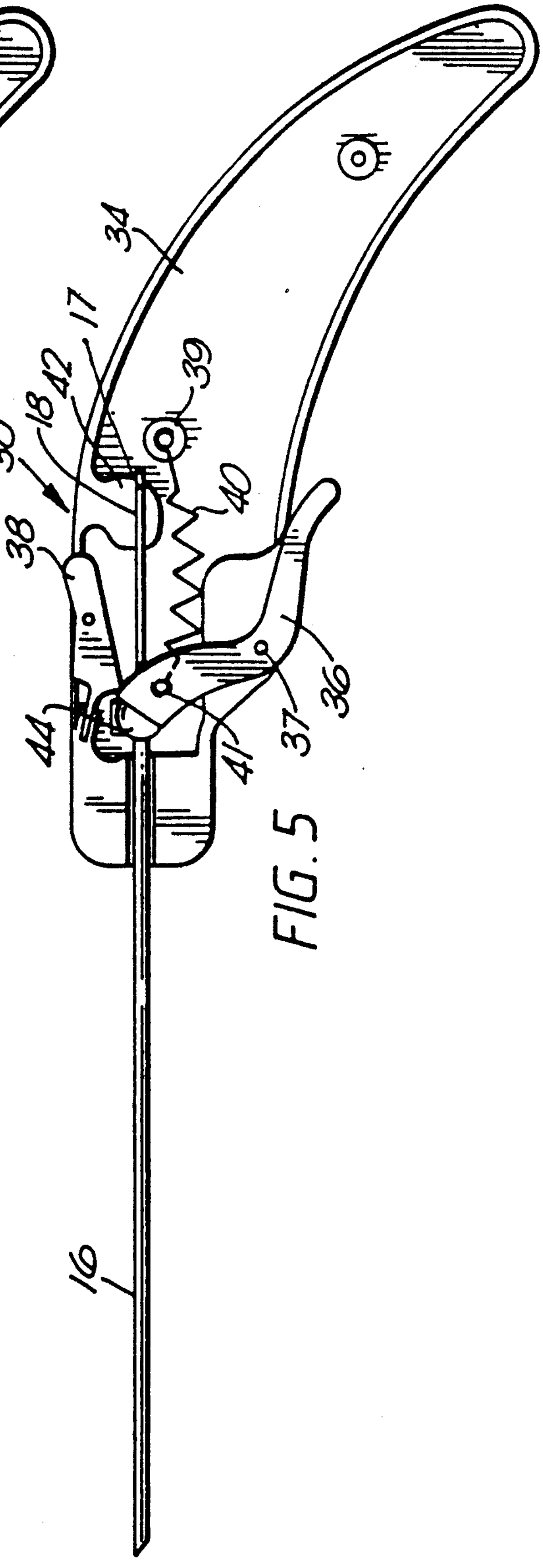
FIG. 5 shows a schematic view of the device in FIG. 3, partly assembled, in a position after use.

To use the device 30 the surgeon drives the sampling needle 18 into the patient and then pulls the lever arm in towards the handle 32,34. This causes the lever arm to pivot about the pivot pin 37 moving the socketed end of the lever arm over the ball 44, thus driving sheath needle 16 along the sampling needle 18 whereby a soft tissue sample is collected. As the lever arm 36 reaches the end of its travel within the handle it pushes past the catch 38 which is biassed by an integral resilient limb 46. As is shown in FIG. 5, once the lever arm 36 has passed the catch 38, the catch drops back down behind the lever arm and the ball 44 preventing accidental removal of the sheath needle 16 from the sampling needle 18.

At all times the surgeon will have used only one hand to collect the soft tissue sample in the sampling needle. Once the sample has been collected the surgeon can use his free hand to support the flesh surrounding the area of penetration whilst the device 30 is withdrawn from the patient. The soft tissue sample is retrieved from the device by releasing the catch 38 which frees the lever arm 36. The lever arm 36 and sheath needle 16 are pulled back to their original position (as shown in FIG. 4) by the spring 40, thus exposing the end of the sampling needle 18 containing the soft tissue sample, and thus allowing the soft tissue sample to be retrieved for further analysis.

Research carried out by the inventor has revealed that in certain circumstances some surgeons and other users of soft tissue biopsy devices prefer to employ an alternative method when using such devices to retrieve soft tissue samples. The alternative preferred method comprises initially driving the sheath needle over the sampling needle and then inserting the thus arranged needles into the patient. Next, the needles are sited at the appropriate location within the patient and the sheath needle is withdrawn to expose the sample collecting slot in the sampling needle and is then driven back fully over the sampling needle to thereby collect a sample of tissue in the sample collecting slot. The device is then removed from the patient to enable the sample to be retrieved.

Trials carried out using this alternative method with the present invention have identified that the force generated by the spring as the trigger is released when the device is first inserted into the patient may be transmitted back into the handle causing the handle and the sampling needle attached thereto to move. It is undesirable for this to happen because if the needle moves it is possible that the tissue sample collected will not be from the correct area required for analysis. In any case, uncontrolled movement of the needle within the patient is likely to at least inflict further discomfort on the patient and could even result in undue injury being caused to the patient in the region from which the sample is being removed.

Figure 6:
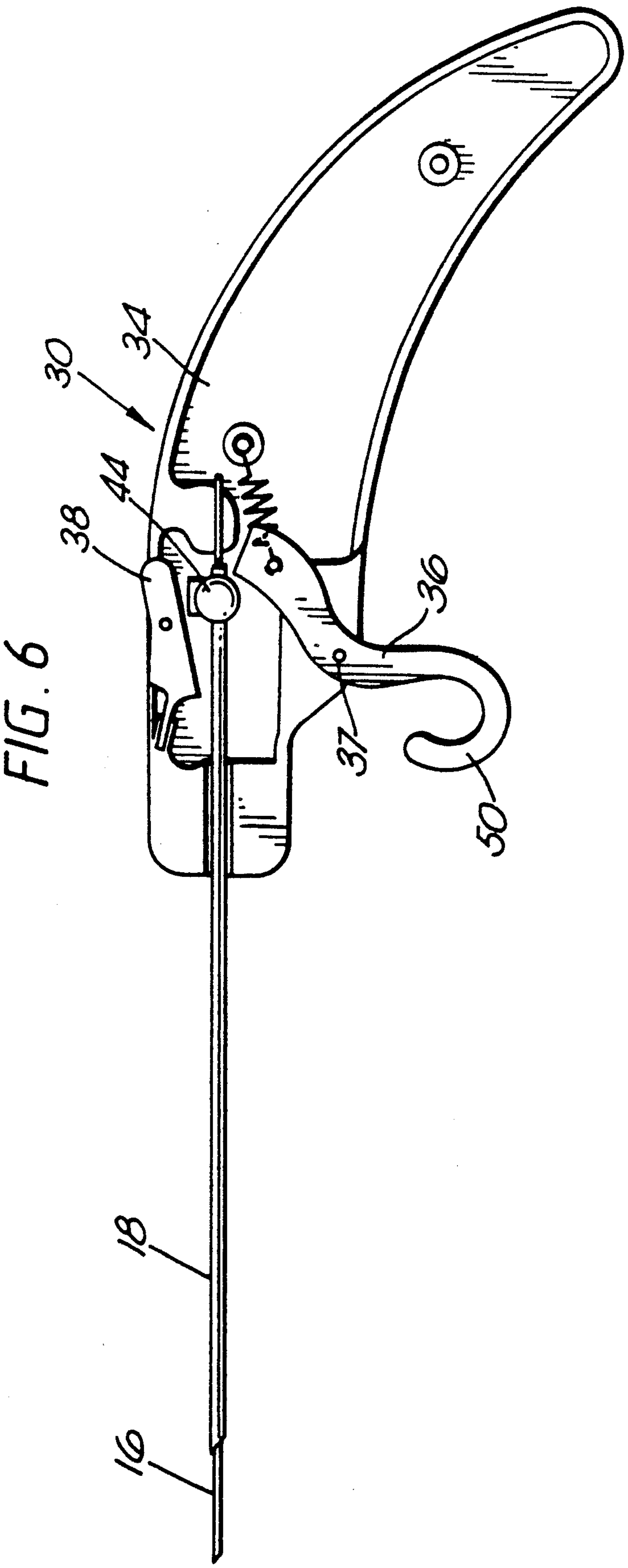
FIG. 6 shows an assembled soft tissue biopsy device in accordance with a second embodiment of the invention.

In another embodiment of the invention, which will now be described with reference to FIG. 6 of the accompanying drawings, the arrangement of the lever arm is altered in order to facilitate use of the device employing the alternative preferred method. In the FIG. 6 embodiment, the lever arm 36 is extended so that the end of the arm below the pivot pin 37, i.e. the end activated by the user, forms a substantially hook shaped portion 50 which receives the end of the user's finger. In providing this arrangement the user gains a greater degree of control over the device when the trigger is released after insertion of the device into a patient when employing the alternative preferred method. The provision of greater control over the device by the user enables the stiffness in the spring to be reduced which substantially obviates the problem of the sample needle 16 moving within the patient when the sheath needle 18 is drawn back by releasing the catch 38. Even where adhesion between the sheath needle 18 and a tissue with a large presence of fatty deposits is large enough to prevent the reduced spring stiffness from drawing the sheath needle back, the provision of the substantially hooked shaped portion 50 facilitates exposure of the collecting portion of the collecting needle 16.

The invention having been described it will be obvious to those skilled in the art that various modifications could be made to the described soft tissue biopsy device without departing from the ambit of the present invention. For example, an embodiment of the invention could be arranged so that the sampling needle is driven by the mechanism and the sheath needle is fixed in the handle. Moreover, the coupling arrangement between the lever arm and sheath needle need not be a ball and socket configuration but may be any other well known and suitable coupling or jointed arrangement. Furthermore, the catch arrangement need not comprise a deadlock type arrangement as described but may instead comprise, for example, a releasable ratchet type arrangement, whereby unintentional unsheathing of the sampling needle may be prevented.

I claim:

1. A device for obtaining a sample of a material from within a larger body of the material, the device comprising: a sampling needle having a sample collecting end portion; a substantially cylindrical outer needle arranged to receive substantially coaxially the sampling needle, the said needles co-operating in use to obtain the sample in the sample collecting end portion;

- a handle means to which one of the said needles is removably secured;
- a lever arm provided in the handle means and arranged to enable the other of the said needles to be slidingly moved in relation to the one needle by a user in order to obtain the sample;
- resilient biassing means provided in the handle means and arranged to bias the lever arm into a predetermined position thereby to position the said needles in a predetermined relationship to each other; and
- a latch means arranged to allow the other of the said needles to be moved to a position in which the sample collecting portion is fully enclosed by the outer needle and to latch the said other needle in the said position.

2. The device according to claim 1 in which the sampling needle is the said one needle and is removably secured at an end portion to the handle means.

3. The device according to claim 1 in which the unsecured end portion of the said one needle comprises a notched portion which forms part of the sample collecting end portion.

4. The device according to claim 1 in which an end of the lever arm innermost of the handle means includes a socket portion which co-operates with a ball portion on the said other need to enable the said other needle to be moved slidingly over the said one needle by the user by way of the lever arm.

5. The device according to claim 4 in which the ball portion comprises a polarising fin and the socket portion comprises a complimentary receiving slot which co-operates with the fin to limit relative rotation between the two said needles.

6. The device according to claim 4 in which the latch member co-operates with the ball portion to latch the other needle in the said position.

7. The device according to claim 1 in which the outermost end of the lever arm comprises a substantially hook shaped end portion which facilitates control of the relative movement of the said needles by the user.

8. The device according to claim 1 in which the latch member comprises a resilient biassing limb which biases the latch member to a position in which the said other needle will be latched.

9. The device according to claim 1 in which the latch member extends through the handle means thereby to enable the user to unlatch the device once a sample has been obtained.

10. The device according to claim 1 in which the latch member co-operates with the lever arm to latch the other needle in the said position.

11. The device according to claim 1 in which the one needle is the sampling needle and the other needle is the outer needle.

12. The device according to claim 1 in which the resilient biassing means is a spring having a predetermined stiffness, and one end of the spring is secured to the lever arm and the other end of the spring is secured to the handle means.

13. The device according to claim 1 in which the said needles are removably provided in the device.

14. The device according to claim 1 supplied for use as a surgical device for obtaining soft tissue biopsy samples from a patient.

15. A surgical device used for example in obtaining a soft tissue biopsy sample from a patient, the surgical device comprising: a handle means; a sampling needle having a sample collecting portion; and a sheath needle co-axially enclosing the sampling needle and having an end portion innermost of the handle means; wherein the handle means includes a sheath needle driving arrangement actuatable by a user, the driving arrangement comprising: a lever arm which has one end extending out from the handle means and another end which co-operates with the said end portion of the sheath needle; resilient biassing means provided in the handle means and arranged to bias the lever arm into a predetermined position thereby to position the said needle in a predetermined relationship to each other; and a latching arrangement for releasably latching the sheath needle in a position where the sample collecting portion of the sampling needle is fully enclosed therein.

* * * * *